US011185287B2

(12) United States Patent
Colliou et al.

(10) Patent No.: US 11,185,287 B2
(45) Date of Patent: Nov. 30, 2021

(54) ADHESIVE OVERLAY (71) Applicant: Vital Connect, Inc., San Jose, CA (US)

(72) Inventors: Olivier Colliou, San Jose, CA (US); Rod Moghadam, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 0 days.

(21) Appl. No.: 16/015,482

(22) Filed: Jun. 22, 2018

(65) Prior Publication Data
US 2019/0388030 A1    Dec. 26, 2019

(51) Int. Cl.
*A61B 5/00* (2006.01)
*A61B 5/145* (2006.01)
*A61B 90/30* (2016.01)

(52) U.S. Cl.
CPC ........ *A61B 5/6833* (2013.01); *A61B 5/68335* (2017.08); *A61B 2090/309* (2016.02); *A61B 2560/0214* (2013.01); *A61B 2560/0412* (2013.01)

(58) Field of Classification Search
CPC ................................ A61B 19/02; A61F 13/02
See application file for complete search history.

(56) References Cited

U.S. PATENT DOCUMENTS

| | | | |
|---|---|---|---|
| 5,662,925 A | 9/1997 | Ebert et al. | |
| 2008/0269657 A1* | 10/2008 | Brenneman | A61F 15/004 |
| | | | 602/41 |
| 2014/0206977 A1 | 7/2014 | Bahney et al. | |
| 2015/0174304 A1* | 6/2015 | Askem | A61M 1/0086 |
| | | | 604/319 |
| 2016/0058380 A1* | 3/2016 | Lee | A61B 5/6832 |
| | | | 600/365 |

FOREIGN PATENT DOCUMENTS

| | | |
|---|---|---|
| CN | 104684595 A | 6/2015 |
| WO | 2018067758 A1 | 4/2018 |

OTHER PUBLICATIONS

"VitalPatch Adhesive Overlay", MediBioSense, Jul. 26, 2019, [online] retrieved from<URL:https://www.youtube.com/watch?v=KCHTjU_nglg>entire document, especially demonstration 1:55-1:35.
International Search Report and Written Opinion from International Application No. PCT/US19/38662 dated Oct. 10, 2019.

* cited by examiner

*Primary Examiner* — Jon Eric C Morales
(74) *Attorney, Agent, or Firm* — Brundidge & Stanger, P.C.

(57) ABSTRACT

A device-securing overlay includes a wearable strip that has a controlled applicant to fit over at least a portion of a wearable device, while an adhesive on an under portion of the wearable strip is placed in contact with at least a top portion of an outer rim of the wearable device as well as a surface upon which the wearable device is placed, without covering portions of the wearable device that require ventilation or an unobstructed view.

13 Claims, 7 Drawing Sheets

ADHESIVE OVERLAY

TECHNICAL FIELD

Described and recited herein are embodiments and/or iterations of removable and/or replaceable adhesive overlays that extend the time for which medical devices, biosensors, etc., may be adhered to a user.

BACKGROUND

Wearable medical sensor devices are used to monitor various aspects of the physical performance and health of users. These devices may be attached directly to the user's skin to then begin collecting physiological data from the user. The collected data may include, but not be limited to, measured heart rates, breathing patterns, body temperature, etc. over an extended period of time. For example, for the sake of accuracy, a patient being observed for cardio-related issues may be required to wear heart monitors for weeks or even months on end; or sleep study subjects may be required to wear biosensors for multiple weeks; etc.

SUMMARY

A wearable device-securing overlay includes a wearable strip that has a controlled applicant to fit over at least a portion of a wearable device, while an adhesive on an under portion of the wearable strip is placed in contact with at least a top portion of an outer rim of the wearable device as well as a surface upon which the wearable device is placed.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION OF PREFERRED EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not intended to be limiting. Other embodiments may be utilized, and other changes may be made, without departing from: the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Described herein are embodiments of an adhesive overlay that may be used to supplement or altogether replace an adhesive or other mechanism provided to adhere a wearable device to a user. The description that follows is intended to enable one of ordinary skill in the art to make and use one or more of the embodiments. Various modifications will be readily apparent to those skilled in the art. Thus, the description is not intended to be so inclusive as to be limited to the described embodiments, but is to be accorded the widest scope consistent with the principles and features described herein.

A wearable medical sensor device may also be referred to, as an example only, a health monitoring sensor device. Examples of such may include a reusable module and a disposable module that each decouple from each other and each comprise varying components to efficiently and continuously monitor a user's health and/or physiological data or, alternatively, administer health-related products or stimulation to the user, e.g., insulin, heat, massage, etc.

Utilizing these wearable medical sensors, a user's physiological data may be collected so that the user's health may be evaluated or, alternatively, apply medicine or stimulation. As an example, such sensors may be utilized to measure an athlete's performance during training or actual competition. The data collected by sensors may include, but not be limited to, heart rate, breathing patterns, body temperature, etc., under certain conditions and/or over an extended period of time. For both the medical patient and the athlete, which are non-limiting examples for whom usage of the embodiments described herein applies, it may be expected that one or more medical sensors are worn, i.e., adhered to the individual's epidermis layer, for an extended period of time and/or under conditions that are not always compatible with long-term adhesion.

For example, for the sake of accuracy, a patient being observed for cardio-related issues may be required to wear one or more heart monitors for weeks or even months on end; or sleep study subjects may be required to wear one or more biosensors for days or weeks without removing the sensor(s); etc. As another example, an athlete in training may be subjected to physiological testing or monitoring that requires the athlete to wear one or more medical sensor devices while training or performing. In both scenarios referenced above, as well as others not explicitly described herein, an adhesive intended to adhere a wearable medical sensor device to the subject's skin, i.e., epidermis layer, may lose its adhesive properties due to, e.g., oil on the patient's skin, the patient having a diaphoretic condition, sweat on the athlete's skin, humidity in the air, the sensor and/or adhesive being removed and re-adhered, etc. As a result, one or more sensors may lose the degree of contact with the user's epidermis layer required for accurate physiological data collection or the sensor(s) may lose contact with the user's body completely.

Thus, a challenge to the dependability, efficacy, and reliability of wearable medical sensor devices that use adhesives to attach the sensor device to the epidermis layer of the subject, e.g., patient or athlete, is limited wear duration. Described herein are adhesive overlay embodiments that make possible extended wear duration for such devices.

Figure 1:
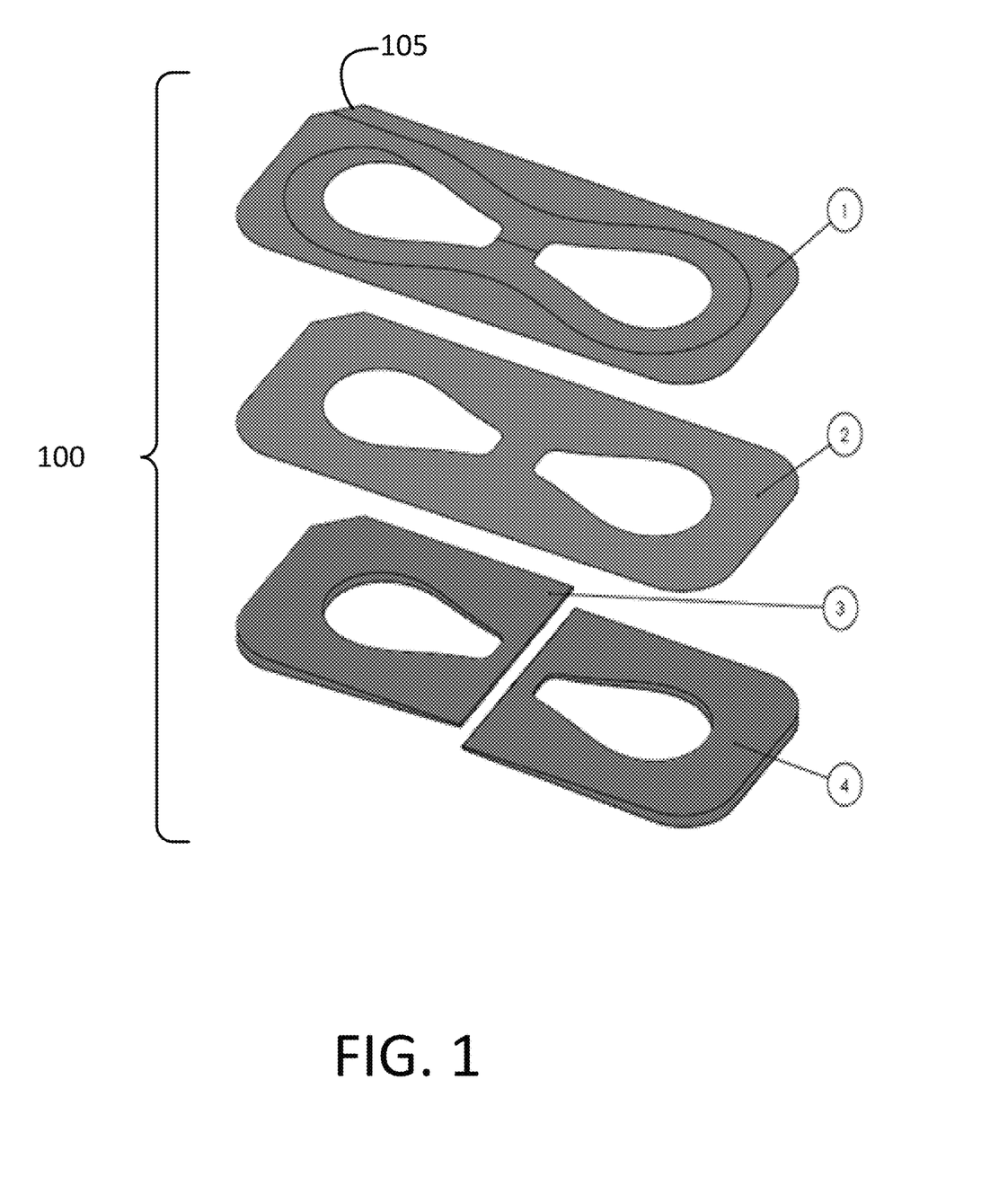
FIG. 1 shows a depiction of the layer features of an adhesive overlay, in accordance with example embodiments described herein.

FIG. 1 shows a depiction of the layer features of adhesive overlay 100, in accordance with example embodiments described herein. As depicted, adhesive overlay 100 includes, at least, cast liner 1, adhesive layer 2, and release liners 3 and 4.

Adhesive overlay 100 may be regarded as a controlled applicant that opens to fit over at least a portion of a device, e.g., a wearable medical sensor device, while an adhesive on an under portion of the wearable strip is placed in contact with at least a top portion of an outer rim of the wearable device and a surface, e.g., skin of a user, upon which the wearable device is placed.

Layers 1-4, which together make up adhesive overlay 100, both corporately and separately, have identical perforations on an interior of each layer. The perforations may have a rippled configuration that allows predetermined portions of the wearable strip to be removed so that a remainder of the wearable strip fits over at least a portion of a wearable medical sensor device, while still maintaining its elastic and adhesive properties. As a non-limiting example of the rippled configuration, each of layers 1-4 may be perforated to accommodate, when the layers are removed along the perforations, a wearable medical sensor device that is 8" in length and 3" in width; each of layers 1-4 may be also be similarly perforated to accommodate a wearable medical device that is 7" in length and 2" in width; and, lastly, each of layers 1-4 may be also be perforated to accommodate a wearable medical device that is 6" in length and 1" in width. In accordance with such example, the perforations to accommodate each successively smaller wearable medical device may be configured inside the perforations to accommodate the immediately larger wearable medical device.

Thus, identical portions of layers 1-4 may be removed in order to fit over all but an outer rim of the subject wearable medical sensor device and adhere to the intended surface, e.g., user's skin. Further, because medical sensor devices of various shapes and sizes may be utilized for a variety of reasons, the rippled configuration of perforations for an embodiment of adhesive overlay 100 may be of various shapes and/or sizes, to provide product versatility.

Cast liner 1 may refer to a layer of a pliable fabric coated with a low-adherent liner to provide packing integrity and rigidity for main adhesive layer 2 prior to application to a user. Main adhesive layer 2 may be a single-sided wearable strip, e.g., TPE tape or PU or bandage, and cast liner 1 may be disposed on the non-coated side of adhesive layer 2. Thus, cast liner 1 may be provided to prevent main adhesive layer 2 from being stretched or otherwise deformed prior to application over a wearable medical sensor device onto an intended surface, e.g., user's skin.

Further, cast liner 1 may facilitate dexterous application on top of a wearable medical sensor by the user, as cast liner 1 is itself temporarily attached to main adhesive layer 2 since the cast layer is the base layer on which the thermoplastic elastomer (TPE) tape or polyurethane (PU) is poured. Although not limiting as an example, cast liner 1 may be configured as a spiral cutout, which includes a tab 105, which is a chamfer on a corner of cast liner 1, serving as the means by which the spiral cutout may be removed. Tab 105 may be grabbed or pinched and then pulled away from the wearable medical sensor device, thus enabling the removal of the entire length of cast liner 1 from main adhesive layer 2 in a manner that is simple and intuitive for the user.

Adhesive layer 2 may refer to a wearable strip made of a carrier material, e.g., a thin polyurethane, that is configured to fit over most of an intended wearable medical sensor device and adhere to both skin and an outer portion of the medical sensor device. Adhesive layer 2 may also be configured to stretch and contort in conformance with the surface, e.g., user's skin, onto which it is adhered. Adhesive layer 2 may be an acrylic adhesive, a single-side PU tape, or a TPU film as well as a non-woven tape, of which an adhesive-coated side contacts the surface of the subject, e.g., the user's skin, and at least an outer rim of the wearable medical sensor device. Alternative embodiments may include a rubber based emulsion adhesive or hydrocolloid. Further, while medical sensor devices may be placed on a subject's skin, such wearable medical sensor devices may alternatively be properly placed on, e.g., the subject's clothing, a plastic or mesh covering, even other sensors or devices, etc.

Release liners 3 and 4 may refer to a layer of a pliable fabric coated with a non-adherent, e.g., siliconized coating or wax, that, when combined, are in contact with at least the entirety of the adhesive side of main adhesive layer 2. That is, while both of release liners 3 and 4 may be intended to cover substantially a respective one-half of the adhesive side of main adhesive layer 2, there may be overlap of either release liner on top of the other. Although release liners 3 and 4 are disposed adjacent to, and possibly partially overlapping with, each other, for the sake of the present description, they are referred to as layers of adhesive overlay 100.

Both of release liners 3 and 4 are configured with prominent "J-fold" style pull tabs to allow easy, i.e., one-handed, removal without requiring a high degree of dexterity. That is, the pull tabs are designed to be prominent enough to be pinched and grabbed by a thumb and forefinger of sizes ranging from child-sized hands to extra-large adult-sized hands. Once held by the user, the respective pull-tab may be removed to expose at least a portion of the adhesive side of adhesive layer 2, which may then be placed on top of at least an outer rim of the wearable medical sensor device and a subject surface, e.g., user's skin.

In accordance with various embodiments, the respective halves covered by release liners 3 and 4 may be lateral or collateral with regard to main adhesive layer 2. Further, alternative embodiments may contemplate a single release liner to cover an entirety of the adhesive side of main adhesive layer 2.

FIG. 2A-2E are depictions of different aspects of an adhesive overlay being applied to a user, in accordance with example embodiments described herein.

As set forth prior, layers 1-4 of adhesive overlay 100, both corporately and separately, have identical perforations on an interior of each layer. The rippled configuration allows predetermined portions of the wearable strip to be removed so that a remainder of the wearable strip fits over at least the portion of a wearable medical sensor device, while still maintaining its elastic and adhesive properties.

Figure 2A:
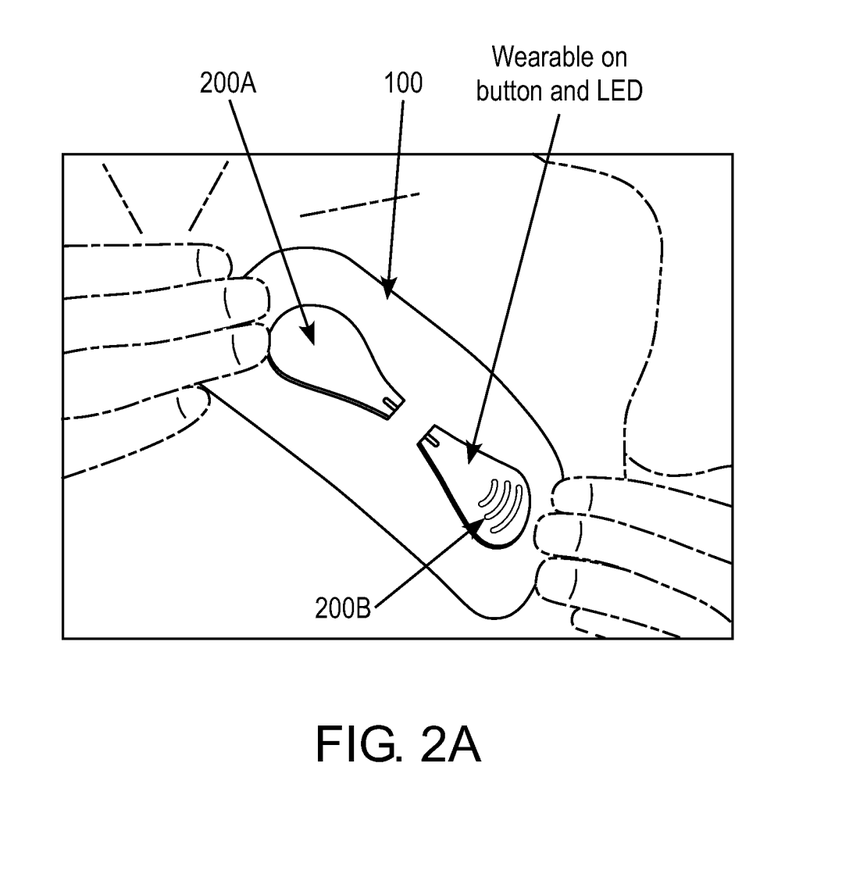
FIG. 2A is a depiction of an aspect of an adhesive overlay being applied to a user, in accordance with example embodiments described herein.

FIG. 2A is a depiction of the self-alignment aspect of the adhesive overlay being applied to a user, in accordance with example embodiments described herein.

As an example only, the depicted wearable medical sensor device 200 is provided in two portions, sensor 200A and battery air vent 200B, while other devices may be provided in one or more portions. Regarding the present example, to align adhesive overlay 100 with wearable medical sensor device 200, portions of the rippled configuration that match the shape of wearable sensor device 200 may be punched out, torn out, or otherwise removed from an interior portion of the layers of adhesive overlay 100. More particularly, by matching the shape of wearable sensor device 200, adhesive overlay 100 may be regarded as self-aligning, thus enabling self-application by even a dexterously challenged user. Accordingly, adhesive overlay 100, including layers 1-4, may be fit over portions 200A and 200B.

Figure 2B:
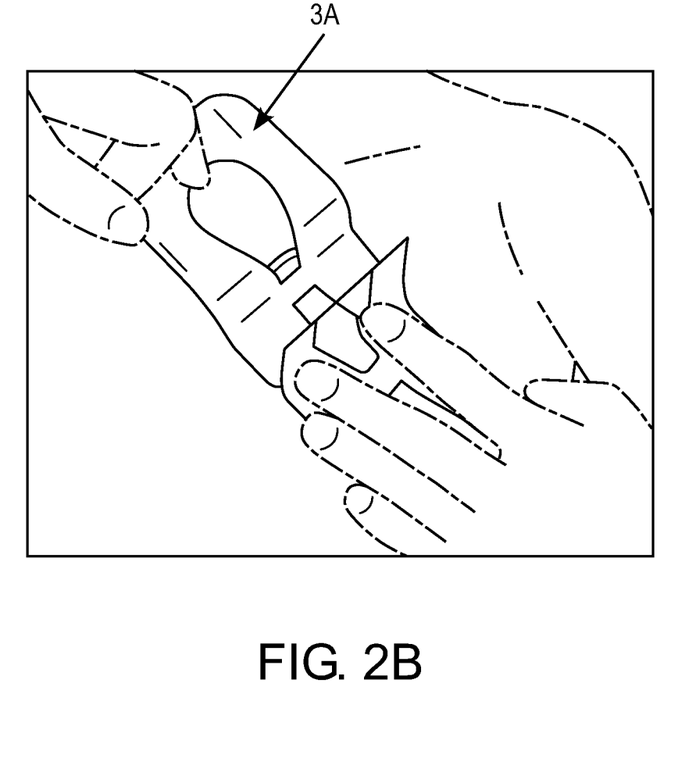
FIG. 2B is a depiction of another aspect of an adhesive overlay being applied to a user, in accordance with example embodiments described herein.
Figure 2C:
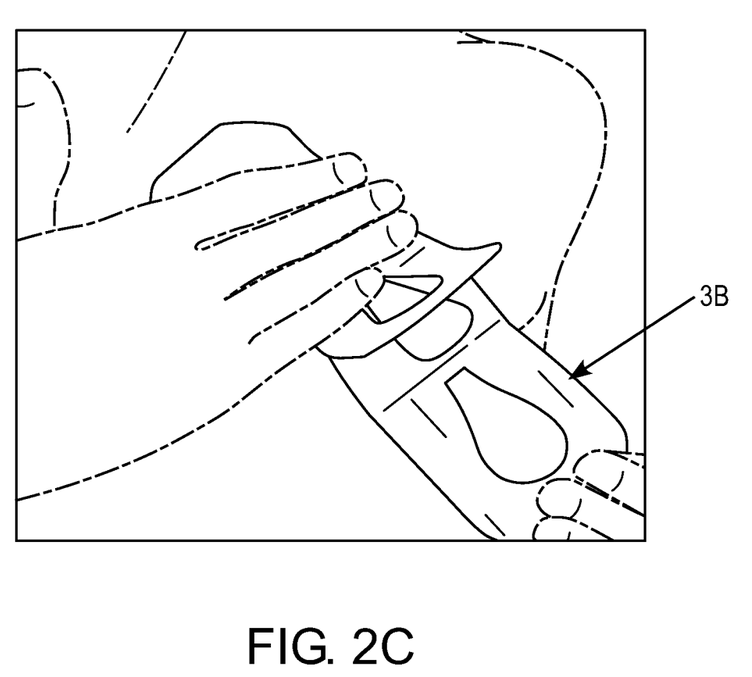
FIG. 2C is a depiction of another aspect of an adhesive overlay being applied to a user, in accordance with example embodiments described herein.

FIGS. 2B and 2C are, respectively, depictions of release liners 3 and 4 being removed using J-fold style pull tabs, that facilitate simple removal without requiring a high degree of dexterity. In FIG. 2B, after adhesive overlay 100 is aligned to fit over portions 200A and 200B, a J-fold release liner 3A may be pinched or grabbed by a user or assistant to lift release liner 3 over sensor portion 200A, thereby exposing the adhesive of main adhesive layer 2, which may then be fit back over sensor portion 200A and evenly applied to the surface to which sensor 200 is applied, e.g., the skin of the user or patient, as well as an outer rim of sensor portion 200A. In FIG. 2C, with main adhesive layer 2 adhered to the surface to which 200 is applied, J-fold release liner 3B may be pinched or grabbed by the user or assistant to lift release liner 4 over sensor portion 200B, thereby exposing the adhesive of main adhesive layer 2, which may then be fit back over sensor portion 200B and evenly applied to the surface to which sensor 200 is applied, e.g., the skin of the user or patient, as well as an outer rim of sensor portion 200B.

Accordingly, cast liner 1 and main adhesive layer 2 remain affixed over wearable medical sensor device 200, having utilized the self-aligning features of adhesive overlay 100, without covering portions of sensor device 200 that require ventilation or to be visually unobstructed, e.g., battery, air vent, power button, LED, etc.

Figure 2D:
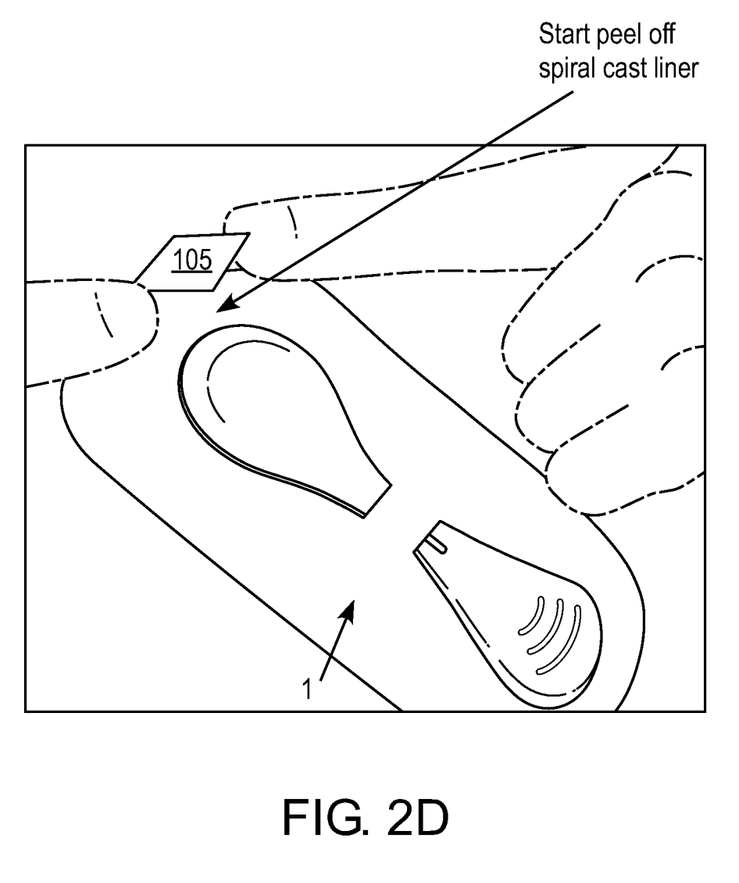
FIG. 2D is a depiction of another aspect of an adhesive overlay being applied to a user, in accordance with example embodiments described herein.
Figure 2E:
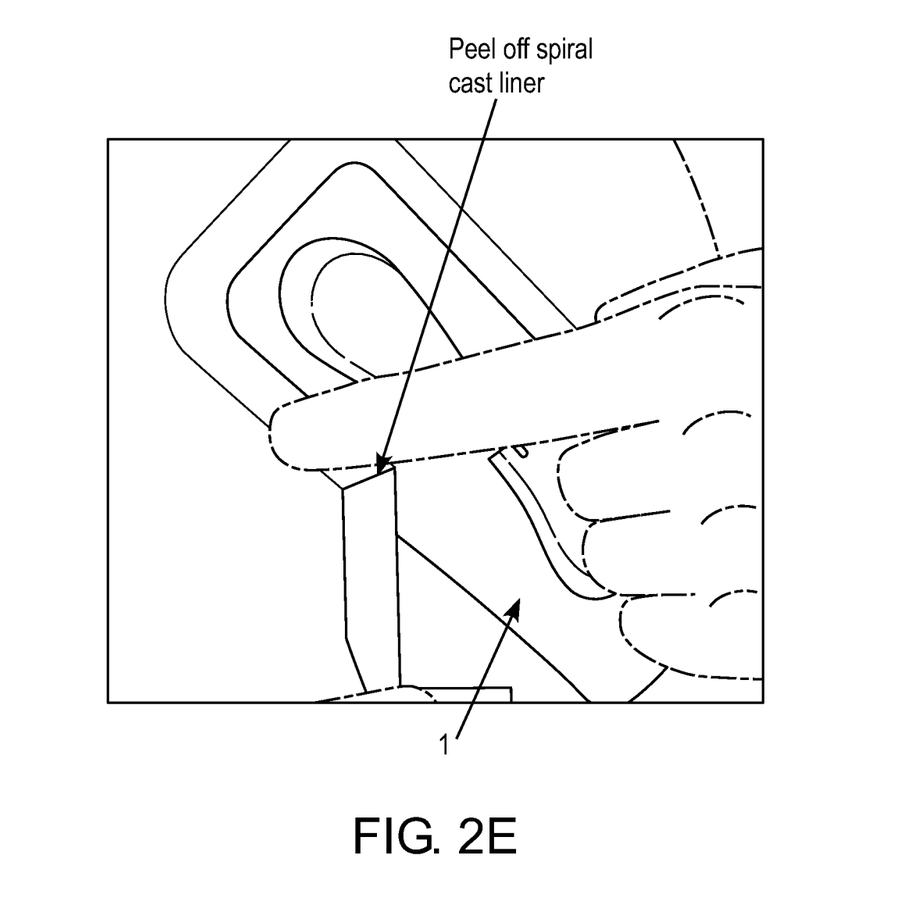
FIG. 2E is a depiction of another aspect of an adhesive overlay being applied to a user, in accordance with example embodiments described herein.

FIGS. 2D and 2E are depictions of cast liner 1 being removed. In FIG. 2D, tab, i.e., chamfer, 105 may be grabbed or pinched by the user or an assistant. In FIG. 2E, chamfer 105 may be pulled away from wearable medical sensor device 200, thus enabling the removal of the entire length of cast liner 1 from main adhesive layer 2 in a manner that is simple and intuitive for the user.

Cast liner 1 provides packing integrity and rigidity for main adhesive layer 2 prior to application. Thus, the removal of cast liner 1, as shown in FIGS. 2D and 2E, enables main adhesive layer 2 to stretch or otherwise conform to a shape and/or movement of the surface to which wearable medical sensor device 200 is applied, e.g., user's skin.

Figure 3:
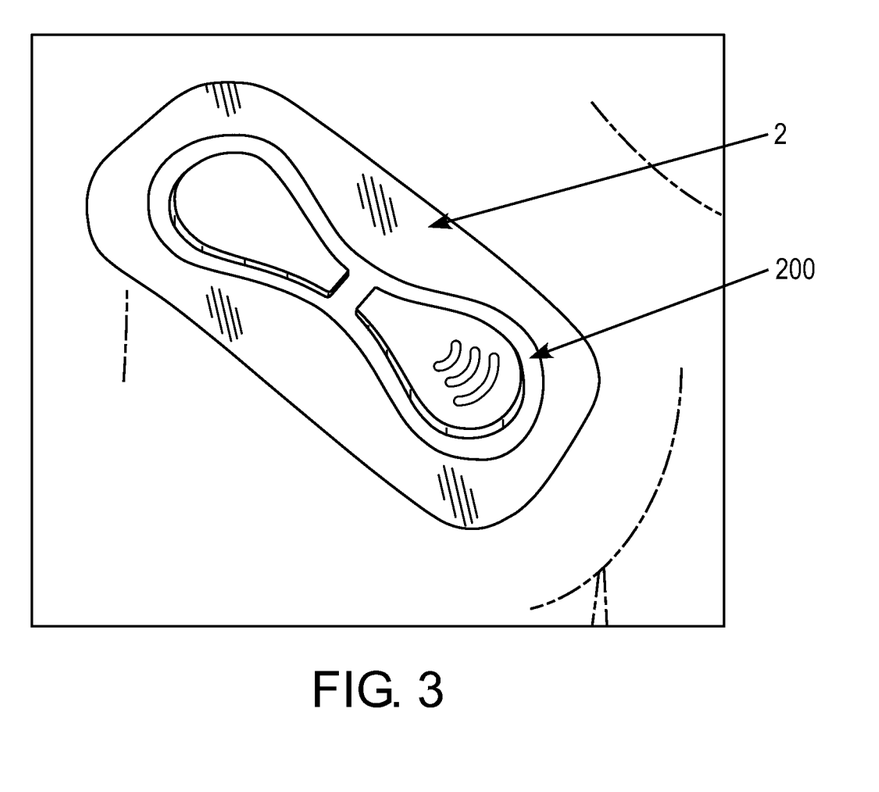
FIG. 3 is a depiction of an adhesive overlay having been applied to a user, in accordance with example embodiments described herein.

FIG. 3 is a depiction of main adhesive layer 2 having been applied to a user, in accordance with example embodiments described herein, affixed over wearable medical sensor device 200, having utilized the self-aligning features of adhesive overlay 100, without covering portions of sensor device 200 that require ventilation or to be visually unobstructed.

In accordance with the depictions and descriptions set forth above, adhesive overlay may supplement or even replace existing adhesives intended to keep wearable medical sensor device 200 in place on the subject surface.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

The invention claimed is:

1. A wearable device-securing overlay, comprising:
 a wearable strip, including a controlled applicant to open the overlay to fit over at least a portion of a wearable device, while an adhesive on an under portion of the wearable strip is placed in contact with at least a top portion of an outer rim of the wearable device and a surface upon which the wearable device is placed,
 wherein the controlled applicant includes:
  a spiral cast liner that is peeled off to render the wearable strip flexible in a manner to match that of the surface upon which the wearable device is placed, and
  a rippled configuration of perforations to allow predetermined portions of the wearable strip to be removed so that a remainder of the wearable strip fits over at least the portion of the wearable device,
 wherein the spiral cast liner includes a chamfer on a corner thereof to facilitate one-handed peeling thereof,
 wherein the wearable strip includes a plurality of overlapping layers, wherein each of the plurality of overlapping layers includes the rippled configuration of perforations to accommodate a successively smaller wearable medical device per removal of a ripple of perforation of the rippled configuration of perforations.

2. The wearable device-securing overlay of claim 1, wherein the surface upon which the wearable device is placed includes an epidermis layer of a user.

3. The wearable device-securing overlay of claim 1, wherein the rippled configuration of perforations respectively accommodate known wearable devices of various sizes.

4. The wearable device-securing overlay of claim 1, wherein the rippled configuration of perforations respectively accommodate known wearable devices of various shapes.

5. The wearable device-securing overlay of claim 1, wherein the controlled applicant includes a j-fold release liner having removable tabs to expose the adhesive on the under portion of the wearable strip.

6. The wearable device-securing overlay of claim 1, wherein the portion of the wearable device over which the overlay fits includes at least one of a power button, a battery, a vent, or an LED light.

7. The wearable device-securing overlay of claim 1, wherein the wearable strip is a polyurethane film.

8. The wearable device-securing overlay of claim 1, wherein the adhesive is an acrylate adhesive.

9. The wearable device-securing overlay of claim 1, wherein the adhesive is a hydrocolloid adhesive.

10. The wearable device-securing overlay of claim 1, wherein the wearable strip is a nonwoven carrier.

11. The wearable device-securing overlay of claim 1, wherein the overlay is replaceable without disrupting adhesion between the wearable device and the surface upon which the wearable device is placed.

12. The wearable device-securing overlay of claim 1, wherein the adhesive is a silicone adhesive.

13. The wearable device-securing overlay of claim 1, wherein the adhesive is a hydrocolloid and acrylate adhesive.

\* \* \* \* \*